(12) United States Patent
Asai (10) Patent No.: US 10,371,647 B2
(45) Date of Patent: Aug. 6, 2019

(54) RADIATION IMAGING APPARATUS AND RADIATION IMAGING SYSTEM

(71) Applicant: CANON KABUSHIKI KAISHA, Tokyo (JP)

(72) Inventor: Hiroki Asai, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 45 days.

(21) Appl. No.: 15/165,119

(22) Filed: May 26, 2016

(65) Prior Publication Data

US 2016/0370304 A1 Dec. 22, 2016

(30) Foreign Application Priority Data

Jun. 22, 2015 (JP) .................................. 2015-125086

(51) Int. Cl.
*G06K 9/00* (2006.01)
*G01N 23/04* (2018.01)

(52) U.S. Cl.
CPC ....... *G01N 23/04* (2013.01); *G01N 2223/401* (2013.01)

(58) Field of Classification Search
None
See application file for complete search history.

(56) References Cited

U.S. PATENT DOCUMENTS

| | | | |
|---|---|---|---|
| 7,822,178 B2 | 10/2010 | Enomoto | |
| 7,994,481 B2 | 8/2011 | Yagi et al. | |
| 2005/0078793 A1* | 4/2005 | Ikeda | A61B 6/00 378/98.8 |
| 2009/0001276 A1 | 1/2009 | Yagi et al. | |
| 2010/0040199 A1 | 2/2010 | Enomoto | |
| 2012/0230469 A1* | 9/2012 | Yamanaka | A61B 6/5205 378/62 |
| 2016/0331340 A1* | 11/2016 | Mako | A61B 6/5258 |

FOREIGN PATENT DOCUMENTS

| | | |
|---|---|---|
| JP | 2007-185375 A | 7/2007 |
| JP | 2008-206971 A | 9/2008 |
| JP | 2010-42150 A | 2/2010 |
| JP | 4557697 B2 | 10/2010 |
| JP | 2010-269083 A | 12/2010 |
| JP | 2012-183241 A | 9/2012 |

OTHER PUBLICATIONS

Co-pending U.S. Appl. No. 15/162,937, filed May 24, 2016.
Office Action dated Apr. 11, 2019, in counterpart application JP 2015-125086 (7 pages).

* cited by examiner

*Primary Examiner* — Atiba O Fitzpatrick
(74) *Attorney, Agent, or Firm* — Venable LLP (57) ABSTRACT

Provided is a radiation imaging apparatus, including: an information outputting unit configured to output state information on a state of the radiation imaging apparatus; a correction data acquiring unit configured to acquire offset correction data through use of image data acquired in an acquisition mode that is set based on the state information; and an image processing unit configured to correct image data acquired by imaging an object through use the offset correction data.

15 Claims, 8 Drawing Sheets

| IMAGING MODE No. | SIZE [cm] | BINNING | FRAME RATE [fps] | OUTPUT GAIN | ACQUISITION MODE |
|---|---|---|---|---|---|
| 1 | 43×43 | 3×3 | 30 | 20 | 1 |
| 2 | 43×43 | 2×2 | 5 | 3 | 0 |
| 3 | 43×43 | 1×1 | 1 | 1 | 0 |
| 4 | 30×30 | 2×2 | 30 | 10 | 1 |
| 5 | 15×15 | 1×1 | 15 | 5 | 1 |
| ⋮ | ⋮ | ⋮ | ⋮ | ⋮ | ⋮ |

FIG. 4A

| STATE INFORMATION No. | STATE |
|---|---|
| 00 | WARMING-UP STATE |
| 01 | TEMPERATURE VARYING STATE |
| 1x | IMAGING READY STATE ACCORDING TO ACQUISITION MODE "1" |

FIG. 4B

| STATE INFORMATION No. | STATE | ACQUISITION MODE INFORMATION |
|---|---|---|
| 00 | WARMING-UP STATE | 0 |
| 01 | TEMPERATURE VARYING STATE | 0 |
| 1x | IMAGING READY STATE ACCORDING TO ACQUISITION MODE "1" | 0, 1 |

| STATE INFORMATION No. | STATE | ACQUISITION MODE INFORMATION |
|---|---|---|
| 000 | WARMING-UP STATE | 0 |
| 001 | TEMPERATURE VARYING STATE | 0 |
| 010 | RELIANCE TIME ELAPSED STATE | 0 |
| 011 | RESIDUAL IMAGE REMAINING STATE | 0 |
| 1xx | IMAGING READY STATE ACCORDING TO ACQUISITION MODE "1" | 0, 1 |

350

RADIATION IMAGING APPARATUS AND RADIATION IMAGING SYSTEM

BACKGROUND OF THE INVENTION

Field of the Invention

The present invention relates to a radiation imaging apparatus and a radiation imaging system, which are used for capturing radiation images.

Description of the Related Art

As radiation imaging apparatus, which are configured to capture a radiation image of an object with the use of radiation (e.g., X ray) transmitted through the object, radiation imaging apparatus capable of displaying a radiation image in real time have been widespread. Further, flat-panel radiation imaging apparatus (FPD) have also been proposed.

The FPD includes minute radiation detectors aligned on a quartz glass substrate in matrix. The radiation detectors each include a lamination of a scintillator configured to convert radiation into visible light and a solid-state photodetector in which an amorphous semiconductor is sandwiched by a transparent conductive film and a conductive film. Further, solid-state photodetectors using a photodetector, e.g., a CCD or a CMOS, have been known. Further, radiation detectors configured to directly detect radiation with solid-state photodetectors without using any scintillator have been known.

The FPD is configured to detect a dose of radiation applied during a given accumulation time as a charge amount. Thus, when a radiation image of an object is captured, if charges irrelevant to application of radiation are present in the radiation detectors, the charges are superimposed on the radiation image as noise, with the result that the image quality of the radiation image is degraded.

For example, as charges causing noise, there are given residual charges that remain, after a radiation image is captured in previous imaging, based on the characteristics of the solid-state photodetectors and the scintillators. Further, as charges causing noise, there is dark current caused by charges generated mainly due to temperatures of the solid-state photodetectors. Besides, fixed noise caused due to defects unique to the radiation detectors is a factor to degrade the image quality of radiation images.

When a radiation image of an object is captured, as accumulation time of an image to which radiation is applied elapses, residual charges and charges of dark current components are also accumulated in proportion to the accumulation time, to thereby degrade the image quality of the radiation image. Thus, an offset correction process is performed in capturing a radiation image of an object in order to remove offset components due to residual charges and dark current charges accumulated during imaging, fixed noise, and other factors.

In general, the offset correction process is performed as follows: image data acquired without radiation application (non-exposure image data) is used as offset correction data, and the offset correction data is subtracted from a radiation image. In this case, capturing of radiation images of an object and acquisition of non-exposure image data (offset correction data) are alternately performed, and the offset correction data is subtracted from the radiation images, to thereby perform the offset correction process. Further, non-exposure image data acquired before capturing of a radiation image of an object is used as offset correction data, and the offset correction data is subtracted from the radiation image, to thereby perform the offset correction process.

When capturing of radiation images of an object and acquisition of non-exposure image data (offset correction data) are alternately performed, while residual images can be reduced, there is a problem in that frame rates are decreased.

When offset correction data is acquired before capturing of a radiation image of an object, while frame rates are increased to enable high-speed continuous image capturing, e.g., moving image capturing, there is a problem in that residual images cannot sufficiently be reduced. Further, dark current charges are changed due to temperatures of the radiation detectors, imaging conditions, or deterioration of sensors with time. Thus, there is a problem in that the accuracy of the offset correction process may not be sufficient when offset correction data is acquired before capturing of a radiation image of an object.

Further, in an ordinary FPD, dark current charges are liable to be unstable immediately after radiation detectors start driving and immediately after radiation application. Further, it has been known that residual charges generated after radiation application greatly change immediately after radiation application is finished. Thus, in order to stably perform the offset correction process, it is necessary to secure a certain period of time from start of driving of the radiation detectors to radiation image capturing or from previous radiation image capturing to next radiation image capturing. Meanwhile, it is desired that radiation images be captured in a short period of time immediately after the driving start or immediately after previous radiation image capturing in order to improve the operability of the radiation imaging apparatus.

In each of Japanese Patent Application Laid-Open No. 2012-183241 and Japanese Patent No. 4557697, there is proposed a technology of determining the stability and a variation amount of offset correction data with respect to time, to thereby acquire offset correction data, in order to maintain the accuracy of an offset correction process.

However, when the temperature of the radiation imaging apparatus changes intensely, e.g., immediately after the radiation imaging apparatus is powered on, the variation amount of the offset correction data becomes larger, and the stability thereof thus deteriorates. Therefore, an acquisition mode of the non-exposure image data, which is used for generating the offset correction data, is automatically chosen disadvantageously. As a result, this acquisition mode chosen automatically may not be an acquisition mode desired by a user.

For example, an acquisition mode of alternately acquiring the radiation image of an object and the non-exposure image data is automatically chosen. In this case, although stable offset correction data can be acquired, the frame rate decreases. Therefore, when the user desires to prioritize a high frame rate over the image quality in the event of an emergency, the related-art radiation imaging apparatus cannot handle this case.

SUMMARY OF THE INVENTION

The present invention has been made in view of the above-mentioned problem, and provides a radiation imaging apparatus capable of performing imaging based on image quality, a frame rate, or the like desired by a user even when a state of the radiation imaging apparatus changes, to thereby enhance usability for the user.

According to one aspect of the present invention, there is provided a radiation imaging apparatus, including: an information outputting unit configured to output state information on a state of the radiation imaging apparatus; a correction data acquiring unit configured to acquire offset correction data from image data acquired in an acquisition mode that is set based on the state information; and an image processing unit configured to correct image data acquired by imaging an object through use the offset correction data.

Further features of the present invention will become apparent from the following description of exemplary embodiments with reference to the attached drawings.

DESCRIPTION OF THE EMBODIMENTS

First Embodiment

Figure 1A:
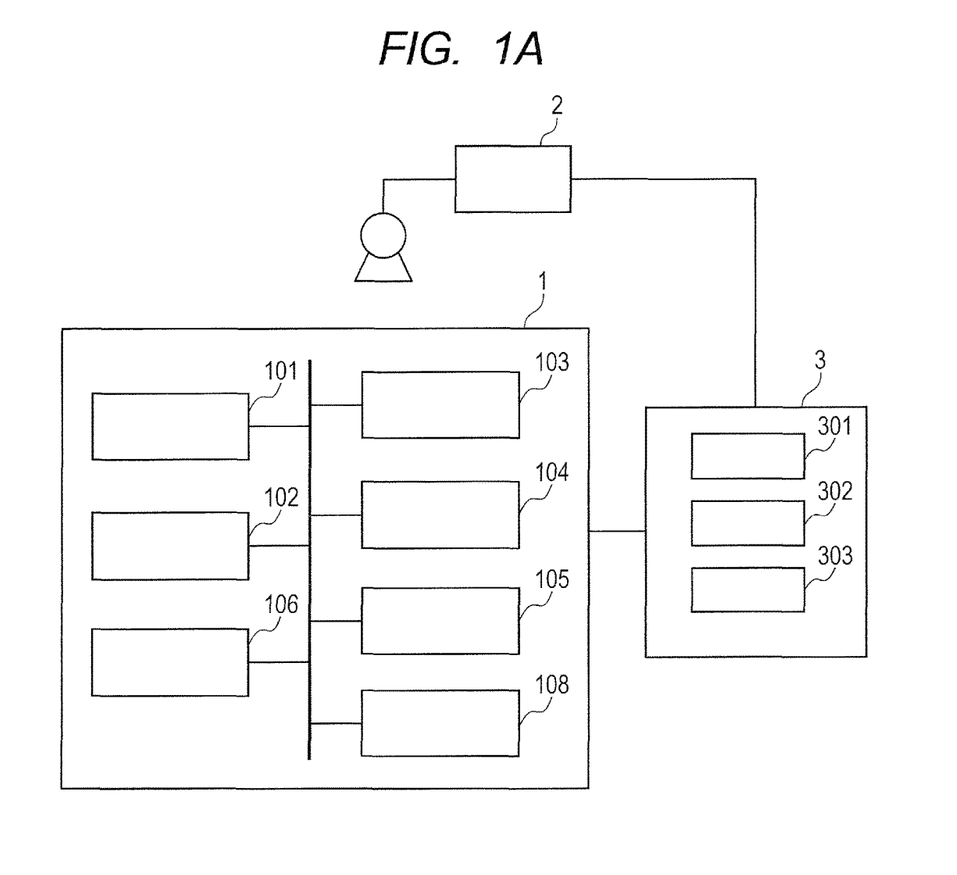
FIG. 1A is a diagram for illustrating an example of a radiation imaging system according to a first embodiment of the present invention.
Figure 1B:
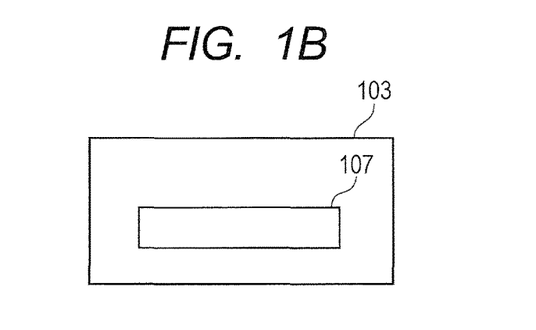
FIG. 1B is a diagram for illustrating an example of a control unit according to a first embodiment of the present invention.

An example of an embodiment of the present invention is described in detail with reference to the drawings. FIG. 1A and FIG. 1B are diagrams for illustrating an example of a radiation imaging system according to this embodiment. As illustrated in FIG. 1A, the radiation imaging system includes a radiation imaging apparatus 1, a radiation generating apparatus 2 configured to apply radiation to the radiation imaging apparatus 1, and a control apparatus 3 configured to control the radiation imaging apparatus 1 and the radiation generating apparatus 2.

The radiation imaging apparatus 1 includes a radiation detecting unit 101, an image processing unit 102, a control unit 103, a storage unit 104, a communication unit 105, a monitoring unit 106, and an information outputting unit 108. As illustrated in FIG. 1B, the control unit 103 includes a correction data acquiring unit 107. The control apparatus 3 includes an input unit 301, a display unit 302, and a communication unit 303.

The radiation detecting unit 101 capable of detecting radiation includes a scintillator, a photodetector array, a driving circuit, a signal amplifying circuit, and an A/D converter, and is configured to generate image data. The signal amplifying circuit is configured to operate based on a gain setting set by a user. The radiation detecting unit 101 includes a plurality of radiation detecting elements configured to generate charges based on a dose of radiation transmitted through an object. The scintillator of the radiation detecting unit 101 has a base material of the scintillator which is excited with radiation having high energy passed through an object, and hence is configured to emit fluorescence in a visible region with recombination energy generated through recombination therein. This fluorescence is emitted by the base material itself, e.g., $CaWO_4$ or $CdWO_4$, or an emission center substance applied to the base material, e.g., CsI:Tl or ZnS:Ag.

The photodetector array is configured to output, through operation of the driving circuit, electric signals corresponding to an amount of fluorescence (a dose of radiation entering the scintillator) detected by each of pixels forming the photodetector array. The A/D converter is configured to convert signals output from the photodetector array into digital values, and output image data.

The image processing unit 102 is configured to subject image data output from the radiation detecting unit 101 to image processing, e.g., an offset correction process. The offset correction process is performed by subtracting, under control of the control unit 103, offset correction data (non-exposure image data) stored in the storage unit 104 from a radiation image (object image) of an object.

Further, the image processing unit 102 may be configured to perform other basic image processing in order to obtain radiation image data having low noise. In addition, the image processing unit 102 may be configured to perform image processing including image quality adjustment that is required by a user, e.g., gradation correction.

The control unit 103 is configured to perform processes relating to control of respective units of the radiation imaging apparatus 1, such as radiation image capturing and communication operation. For example, the control unit 103 is configured to give the driving circuit of the radiation detecting unit 101 instructions to acquire a radiation image, and give the storage unit 104 instructions to store the acquired radiation image. Further, the control unit 103 is configured to set an acquisition mode for acquiring the image data (non-exposure image data) through use of a table stored in the storage unit 104.

Further, the control unit 103 is configured to transmit/receive data (image data, control signals, and other data) to/from the control apparatus 3 via the communication unit 105, and perform various processes based on the received data. For example, the control unit 103 is configured to read a program or other data stored in the storage unit 104, and control the radiation imaging apparatus 1 based on the program or other data. Further, the radiation imaging apparatus 1 may be controlled by a control signal generating circuit formed, for example, of an ASIC, or may be controlled by both of a program and a control circuit.

The storage unit 104 is configured to store information such as image data output from the radiation detecting unit 101 or the image processing unit 102, image data for the correction processes of the image processing unit 102 (offset correction data, gain correction data, and other data), imaging mode information, acquisition mode information (e.g., a table for setting the acquisition mode), and log information representing results of internal processing.

Further, when the control unit 103 is the one using software, e.g., a CPU, the storage unit 104 is configured to also store the software. The storage unit 104 can be implemented without any specific restriction, and the storage unit 104 may be implemented by one or a plurality of memory devices or HDDs, a volatile or non-volatile storage unit, or the combination thereof.

The communication unit 105 is implemented with the use of a wireless LAN, a wired LAN, or a communication module for public networks, and is configured to transfer various kinds of data (image data subjected to the image processing in the image processing unit 102, and log information) to the outside. For example, the communication unit 105 is configured to communicate to/from the control apparatus 3.

The monitoring unit 106 includes a temperature sensor and a timer. The monitoring unit 106 is configured to monitor, as monitoring information, at least one of temperature of the radiation imaging apparatus 1, a length of time that has elapsed since the radiation imaging apparatus 1 was powered on, a length of time that has elapsed since the radiation imaging apparatus 1 acquired the offset correction data, a length of time that has elapsed since the radiation imaging apparatus 1 captured an exposure image, or a length of time that has elapsed since the radiation imaging apparatus 1 captured a non-exposure image.

As used herein, the term "non-exposure image data" refers to image data acquired by the radiation imaging apparatus 1 under a state in which radiation is applied, and the term "non-exposure image data" refers to image data acquired by the radiation imaging apparatus 1 under a state in which radiation is not applied.

The correction data acquiring unit 107 is configured to acquire the offset correction data through use of image data (non-exposure image data) acquired in an acquisition mode that is set based on state information on a state of the radiation imaging apparatus 1, and to store the acquired offset correction data in the storage unit 104. The correction data acquiring unit 107 may be configured to acquire the offset correction data through use of a plurality of pieces of image data. For example, the correction data acquiring unit 107 may be configured to acquire an average of a plurality of pieces of non-exposure image data as the offset correction data. The image processing unit 102 is configured to correct image data (radiation image data) acquired by imaging an object through use of the offset correction data.

The information outputting unit 108 is configured to output the state information on the state of the radiation imaging apparatus 1 based on at least one of the temperature of the radiation imaging apparatus 1, the length of time that has elapsed since the radiation imaging apparatus 1 was powered on, the length of time that has elapsed since the radiation imaging apparatus 1 acquired the offset correction data, the length of time that has elapsed since the radiation imaging apparatus 1 captured the exposure image, the length of time that has elapsed since the radiation imaging apparatus 1 captured the non-exposure image, or how much a residual image remains in an image captured by the radiation imaging apparatus 1 (the degree of the residual image).

In this case, the information outputting unit 108 is configured to output, as the state information, at least one of a warming-up state of the radiation imaging apparatus 1, an equilibrium state of the radiation imaging apparatus 1, a temperature varying state of the radiation imaging apparatus 1, an imaging ready state of the radiation imaging apparatus 1 according to a predetermined acquisition mode, a reliance time elapsed state of the offset correction data of the radiation imaging apparatus 1, or a residual image remaining state of the radiation imaging apparatus 1.

Further, the information outputting unit 108 is configured to output acquisition mode information on the acquisition mode depending on the state of the radiation imaging apparatus 1 (based on the state information). In this case, when the acquisition mode that is based on the state information and the acquisition mode that is set for the radiation imaging apparatus 1 are different from each other, the information outputting unit 108 outputs notice information for notifying that the acquisition modes are different from each other.

The information outputting unit 108 may be configured to output, as the acquisition mode information, at least one of an acquisition mode of acquiring the image data (non-exposure image data) before the imaging of the object or an acquisition mode of acquiring the image data (non-exposure image data) after the imaging of the object. The information outputting unit 108 may also be configured to output, as the acquisition mode information, an acquisition mode of alternately performing the imaging of the object and the acquisition of the offset correction data through use of image data acquired after the imaging of the object.

The control apparatus 3 is configured to display captured images, receive imaging orders, and input imaging information. The control apparatus 3 includes the input unit 301 with which a user can input various kinds of data, the display unit 302 configured to display, for example, a setting screen for setting the imaging mode, the acquisition mode, and others, and radiation images, and the communication unit 303 configured to transmit/receive data to/from the radiation imaging apparatus 1.

The input unit 301 is used for receiving operation from the user. The input unit 301 can be implemented without any specific restriction as long as the input unit 301 can receive inputs from the user. For example, the input unit 301 is realized by various switches, a keyboard, and a touch panel that are operated by the user.

The display unit 302 is configured to display, for example, a setting screen for setting the imaging mode, the acquisition mode, and others, and the radiation image received from the radiation imaging apparatus 1, and to notify the user of the state of the radiation imaging apparatus 1. Further, in this embodiment, the display unit 302 functions as a notification unit, and is configured to notify the user of the state information and the notice information output by the information outputting unit 108. The display unit 302 is implemented without any specific restriction, and is realized by, for example, an LED, an LCD, and a monitor.

The communication unit 303 is used for communication between the communication unit 105 of the radiation imaging apparatus 1 and the control apparatus 3, and is configured to acquire image data output from the radiation imaging apparatus 1, and control data communication between the radiation imaging apparatus 1 and the control apparatus 3. The communication unit 303 is implemented without any specific restriction, and is realized with the use of a wireless LAN, a wired LAN, or a communication module for public networks.

Figure 2:
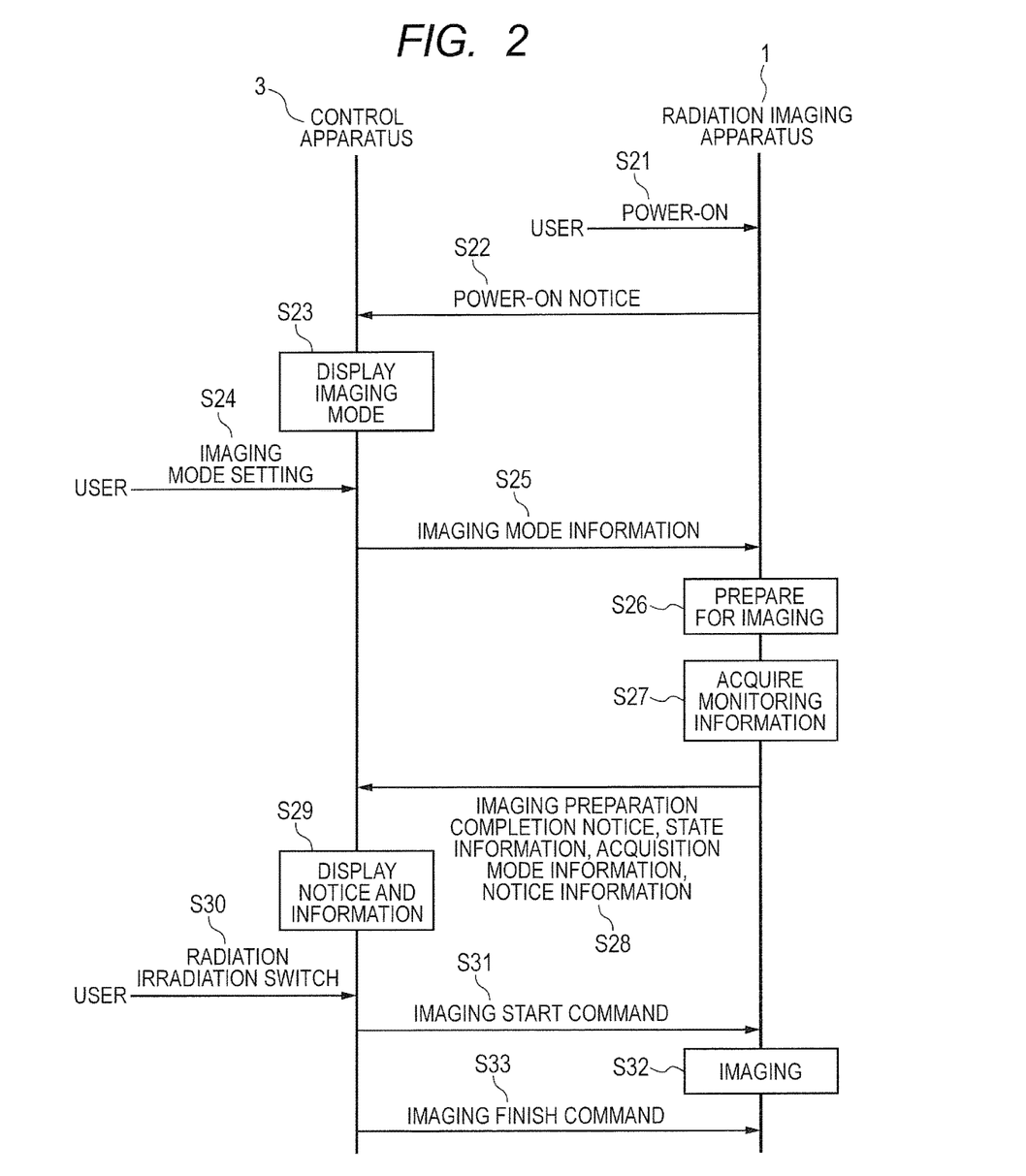
FIG. 2 is a sequence diagram for illustrating operations to be performed from power-on of a radiation imaging apparatus to completion of imaging.

Next, referring to FIG. 2, operations of the radiation imaging apparatus 1 and the control apparatus 3 are described in detail. FIG. 2 is a sequence diagram for illustrating operations to be performed from power-on of the radiation imaging apparatus 1 to completion of imaging.

In Step S21, the user turns on the power of the radiation imaging apparatus 1, and the radiation imaging apparatus 1 is powered on as a result. In Step S22, the radiation imaging apparatus 1 notifies the control apparatus 3 that the radiation imaging apparatus 1 is powered on. In Step S23, when receiving the power-on notice of the radiation imaging apparatus 1, the display unit 302 of the control apparatus 3 displays an input screen for inputting the imaging mode. In Step S24, the user uses the input unit 301 of the control apparatus 3 to set an imaging mode suited to an imaging technique through the setting screen of the display unit 302.

In Step S25, the control apparatus 3 transmits, via the communication unit 303, the imaging mode information on the set imaging mode to the radiation imaging apparatus 1. The control unit 103 receives the imaging mode information from the control apparatus 3, and sets the acquisition mode for acquiring the image data (non-exposure image data).

Figure 3:
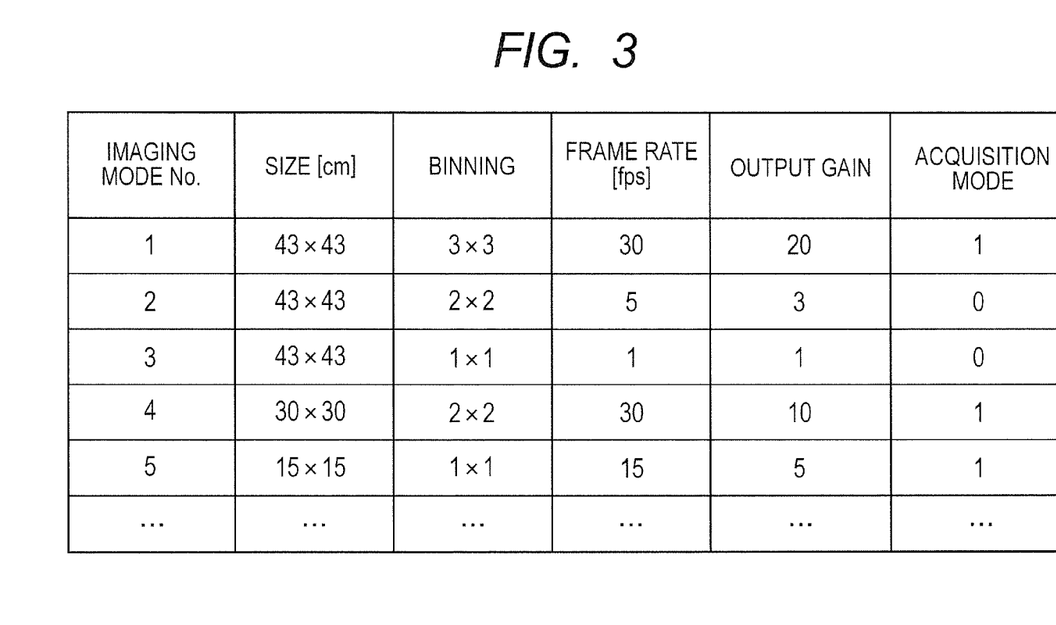
FIG. 3 is a table for showing an example of setting parameters included in imaging mode information.

FIG. 3 is a table for showing an example of setting parameters included in the imaging mode information. As shown in FIG. 3, the imaging mode information includes an imaging mode No., the size of an image, binning, a frame rate, an output gain, and an acquisition mode. The acquisition mode is a mode for acquiring the image data (non-exposure image data), and is indicated as "0" or "1" in FIG. 3.

Herein, the acquisition mode of "0" is an acquisition mode of acquiring the image data (non-exposure image data) immediately before or immediately after the imaging of the object. Further, the acquisition mode of "0" is an acquisition mode of alternately performing the imaging of the object and the acquisition of the offset correction data. In this case, the image processing unit 102 alternately performs the capturing of the radiation image of the object and the acquisition of the image data (non-exposure image data), and subtracts the image data (non-exposure image data) acquired after the imaging of the object from the radiation image of the object, to thereby perform an offset correction process.

The acquisition mode of "1" is an acquisition mode of acquiring image data (non-exposure image data) in advance before imaging of an object. In this case, there is no need to acquire the image data (non-exposure image data) every time the object is imaged. The image processing unit 102 subtracts the image data (non-exposure image data) acquired as the offset correction data before the imaging of the object from the radiation image of the object, to thereby perform the offset correction process.

In Step S26, the control unit 103 prepares for the imaging by the radiation imaging apparatus 1 based on the set imaging mode information. In Step S27, the information outputting unit 108 acquires the monitoring information from the monitoring unit 106.

In Step S28, when the preparation for all of the set imaging modes is completed, the information outputting unit 108 notifies the control apparatus 3 that the preparation for the imaging is completed. At this time, the information outputting unit 108 outputs, based on the monitoring information acquired in Step S27, the state information on the state of the radiation imaging apparatus 1 to the control apparatus 3. When receiving the notice that the preparation for the imaging is completed, the control apparatus 3 enables the capturing of the radiation image of the object in the imaging mode for which the preparation is completed.

Figure 4A:
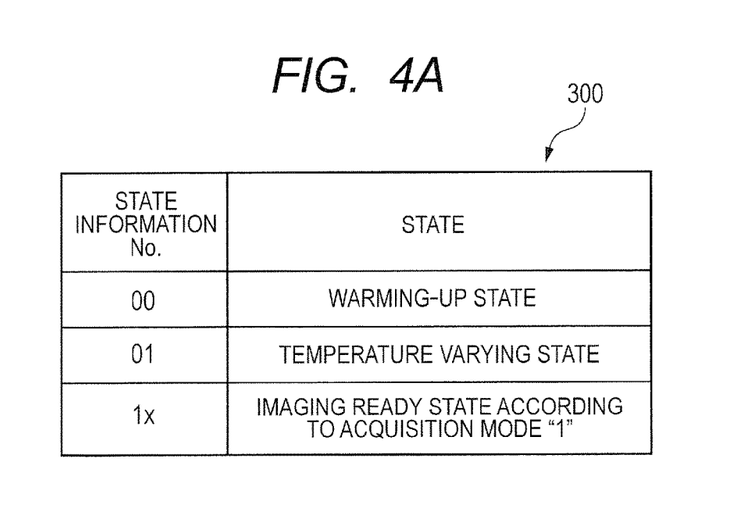
FIGS. 4A and 4B are tables for showing examples of state information according to the first embodiment.

FIG. 4A and FIG. 4B are tables for showing examples of the state information. State information 300 of FIG. 4A includes a state information No. and the state of the radiation imaging apparatus 1. For example, based on the temperature of the radiation imaging apparatus 1 and the length of time that has elapsed since the radiation imaging apparatus 1 was powered on, the information outputting unit 108 outputs the state information 300 including the warming-up state of the radiation imaging apparatus 1, the temperature varying state thereof, or the imaging ready state thereof according to the acquisition mode "1" (equilibrium state).

Figure 4B:
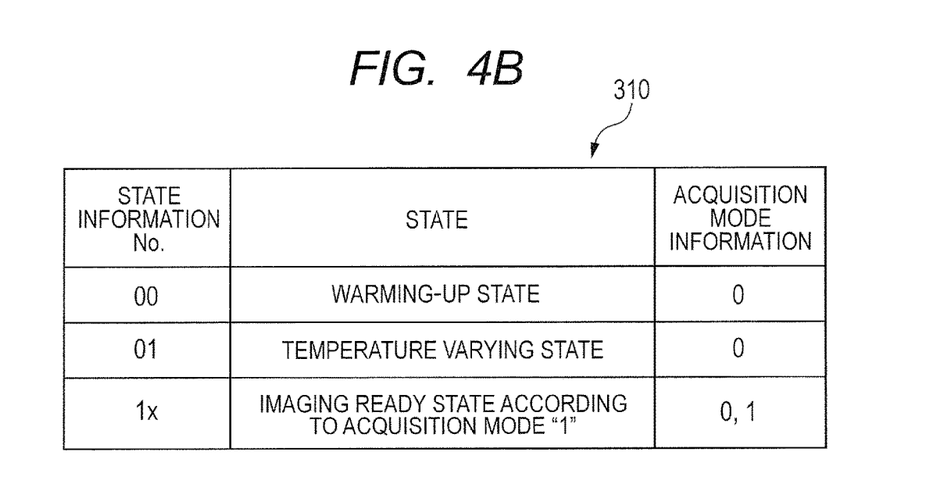

Further, state information 310 of FIG. 4B includes the acquisition mode (acquisition mode information) corresponding to the radiation imaging apparatus 1. For example, the information outputting unit 108 outputs the acquisition mode "0" corresponding to the warming-up state and the temperature varying state of the radiation imaging apparatus 1. Further, the information outputting unit 108 outputs the acquisition modes "0" and "1" corresponding to the imaging ready state according to the acquisition mode "1" (equilibrium state). As described above, the information outputting unit 108 may output the acquisition mode information on the acquisition mode depending on the state of the radiation imaging apparatus 1 (based on the state information).

Further, in Step S28, when the acquisition mode that is based on the state information 310 and the acquisition mode that is set by the control unit 103 based on the imaging mode information are different from each other, the information outputting unit 108 may output the notice information for notifying that the acquisition modes are different from each other.

Figure 5:
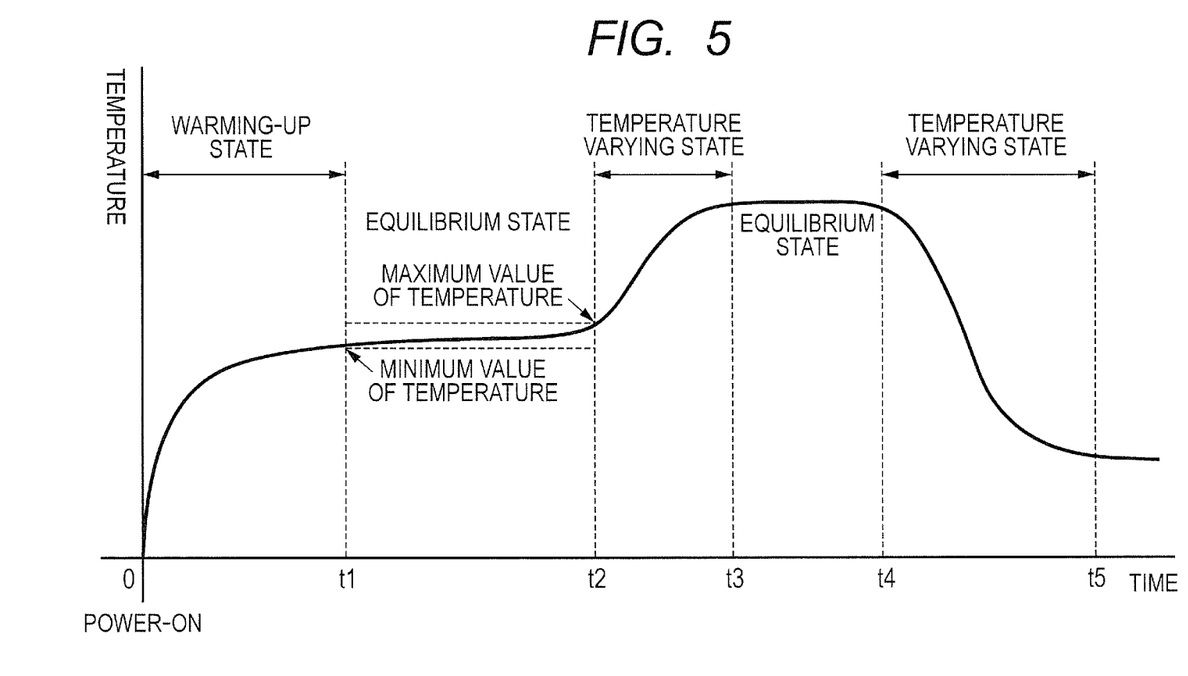
FIG. 5 is a graph for showing an example of determination on a state of the radiation imaging apparatus.

FIG. 5 is a graph for showing an example of determination on the state of the radiation imaging apparatus 1. As shown in FIG. 5, when the length of time that has elapsed since the radiation imaging apparatus 1 was powered on is less than a predetermined threshold t1, the information outputting unit 108 determines that the radiation imaging apparatus 1 is in the warming-up state. Alternatively, when the temperature of the radiation imaging apparatus 1 is less than a predetermined threshold, the information outputting unit 108 determines that the radiation imaging apparatus 1 is in the warming-up state.

Further, when a change over time of the temperature of the radiation imaging apparatus 1 (e.g., a time derivative of temperature) is less than a predetermined threshold, the information outputting unit 108 determines that the radiation imaging apparatus 1 is in the equilibrium state. On the other hand, when the change over time of the temperature of the radiation imaging apparatus 1 (e.g., the time derivative of temperature) is equal to or greater than the predetermined threshold, the information outputting unit 108 determines that the radiation imaging apparatus 1 is in the temperature varying state.

Alternatively, when a difference between a maximum value and a minimum value of the temperature of the radiation imaging apparatus 1 within a predetermined period of time is less than a predetermined threshold, the information outputting unit 108 determines that the radiation imaging apparatus 1 is in the equilibrium state. On the other hand, when the difference between the maximum value and the minimum value of the temperature of the radiation imaging apparatus 1 within the predetermined period of time is equal to or greater than the predetermined threshold, the information outputting unit 108 determines that the radiation imaging apparatus 1 is in the temperature varying state.

Alternatively, when the temperature of the radiation imaging apparatus 1 within a predetermined period of time falls within a predetermined range, the information outputting unit 108 determines that the radiation imaging apparatus 1 is in the equilibrium state. On the other hand, when the temperature of the radiation imaging apparatus 1 within the predetermined period of time falls beyond the predetermined range, the information outputting unit 108 determines that the radiation imaging apparatus 1 is in the temperature varying state.

In this case, as the predetermined range of temperature, a maximum value and a minimum value of the temperature obtained under a state in which the change over time of the temperature is less than the predetermined threshold (equilibrium state) may be set as an upper limit and a lower limit of the predetermined range, respectively. As another example, as the predetermined range of temperature, the upper limit and the lower limit thereof may be set with an average of the temperature obtained under the state in which the change over time of the temperature is less than the predetermined threshold, the average being the center of the range.

As described above, the information outputting unit 108 sets the threshold based on the temperature change of the radiation imaging apparatus 1 and compares the temperature of the radiation imaging apparatus 1 to the threshold, to thereby output the state information.

A position where the temperature of the radiation imaging apparatus 1 is to be measured may be a surface of a control board of the radiation imaging apparatus 1, or may be an internal surface of a housing of the radiation imaging apparatus 1. Further, examples of a factor causing the temperature change of the radiation imaging apparatus 1 include a change in room temperature due to turning on or off of an air conditioner, a change in room temperature due to opening or closing of a window or a door, and a change in heat generation due to a power saving mode (sleep mode) of the radiation imaging apparatus 1.

In Step S29, the control apparatus 3 receives, along with the imaging preparation completion notice, the state information (including the acquisition mode information) and the notice information, and the display unit 302 of the control apparatus 3 functions as the notification unit to display the imaging preparation completion notice, the state information (including the acquisition mode information), and the notice information.

Figure 6:
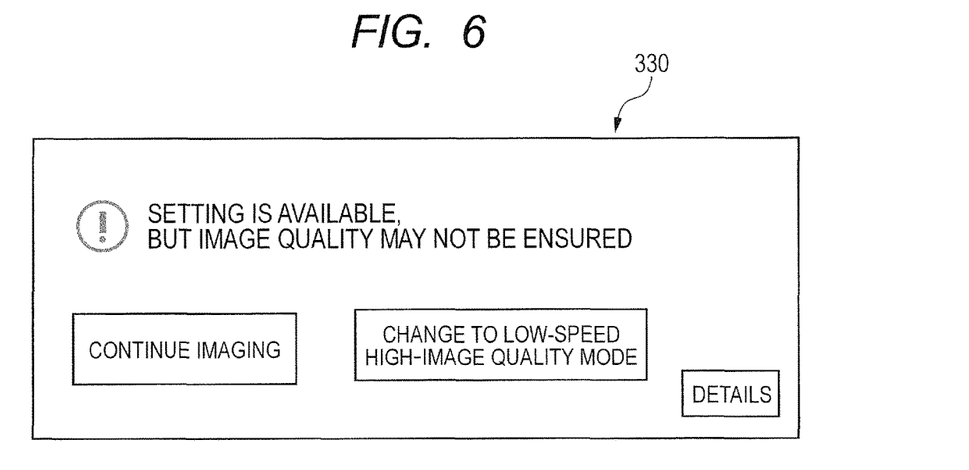
FIG. 6 is a diagram for illustrating an example of a warning to be displayed on a display unit.

For example, when the control apparatus 3 has received the state information "1×" shown in FIG. 4A and FIG. 4B in a case where the control unit 103 sets the acquisition mode "1" in accordance with the imaging mode information of FIG. 3, the display unit 302 displays the imaging preparation completion notice without displaying the state information and the notice information. On the other hand, when the control apparatus 3 has received the state information "00" or "01" shown in FIG. 4A and FIG. 4B or has received the notice information in this case, the display unit 302 displays a warning (notice information). FIG. 6 is a diagram for illustrating an example of the warning to be displayed on the display unit 302. As illustrated in FIG. 6, depending on the state of the radiation imaging apparatus 1, a warning 330 is displayed, in which a screen for choosing the acquisition mode is displayed.

In Step S30, when the user presses a radiation irradiation switch, the radiation generating apparatus 2 applies radiation to the radiation imaging apparatus 1. In Step S31, when the user presses the radiation irradiation switch, the control apparatus 3 transmits a command to start imaging to the radiation imaging apparatus 1, and transmits to the radiation imaging apparatus 1 the acquisition mode chosen in accordance with the state information (including the acquisition mode information) and the notice information.

In Step S32, the radiation imaging apparatus 1 starts capturing the radiation image of the object in accordance with the acquisition mode chosen depending on the state of the radiation imaging apparatus 1. In Step S33, when the user finishes pressing the radiation irradiation switch, the control apparatus 3 transmits a command to finish the imaging to the radiation imaging apparatus 1, and then the radiation imaging apparatus 1 stops the imaging.

As described above, by outputting the state information on the state of the radiation imaging apparatus to choose the acquisition mode, even when a temperature change of the radiation imaging apparatus is intense, imaging based on the image quality, the frame rate, or the like desired by the user is enabled. As a result, usability for the user can be enhanced.

Second Embodiment

An example of an embodiment of the present invention is described in detail with reference to the drawings. Descriptions of the same configurations, functions, and operations as those of the first embodiment described above are omitted, and differences from this embodiment are mainly described.

Figure 7A:
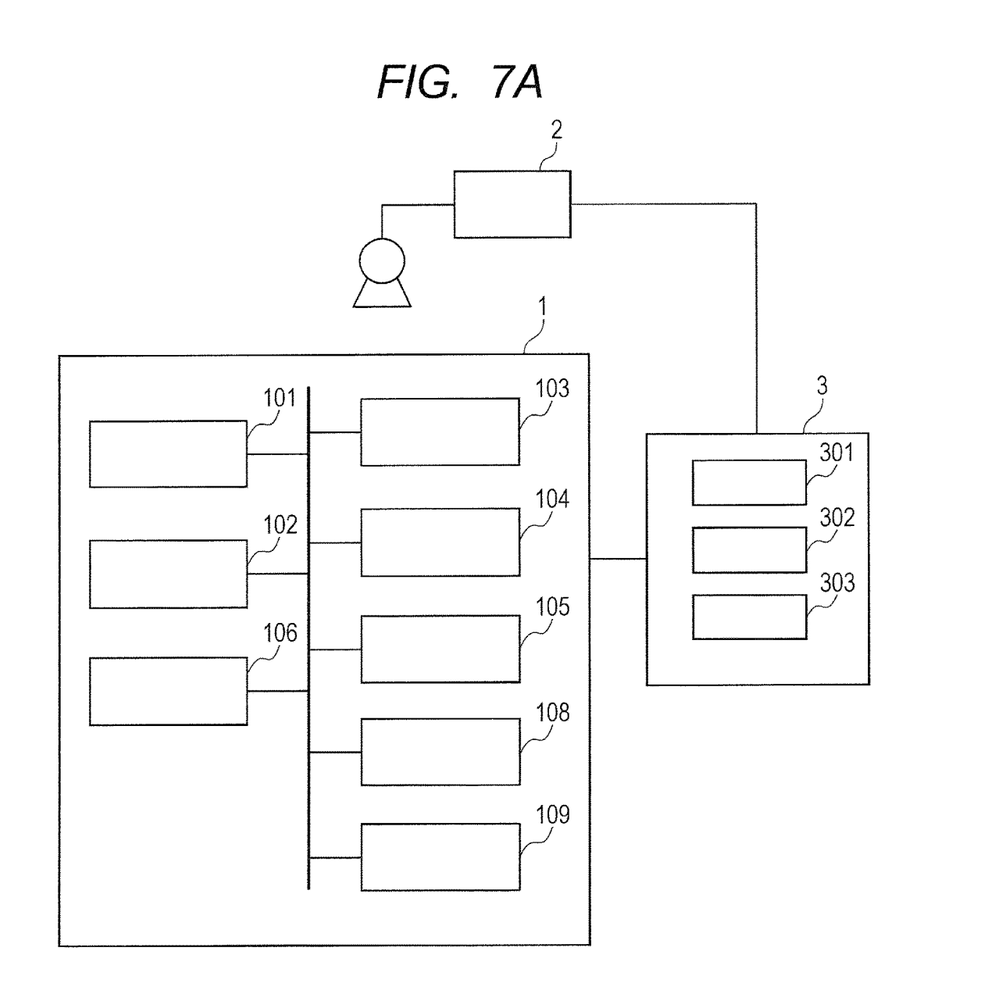
FIGS. 7A and 7B are diagrams for illustrating an example of a radiation imaging system according to a second embodiment of the present invention.
Figure 7B:
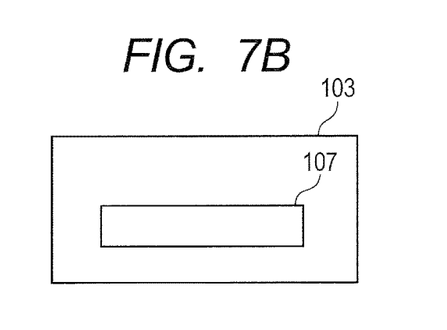

FIGS. 7A and 7B are diagrams for illustrating an example of a radiation imaging system according to this embodiment. As illustrated in FIG. 7A, in the radiation imaging system, the radiation imaging apparatus 1 further includes an image analyzing unit 109.

The image analyzing unit 109 is configured to monitor, as the monitoring information, how much a residual image remains in the image captured by the radiation imaging apparatus 1 (e.g., the radiation image, the exposure image, and the non-exposure image of the object), i.e., to monitor the degree of the residual image. For example, when the imaging mode is transmitted from the control apparatus 3 to the radiation imaging apparatus 1, the image analyzing unit 109 monitors whether or not a residual image remains in the radiation image of the object or the offset correction data. To analyze the residual image, various methods that are commonly known are applicable.

For example, during a period from the stop of radiation application to the next start of radiation application, the image analyzing unit 109 monitors a statistical value of an output signal of each of the radiation detecting elements of the radiation detecting unit 101, and determines whether or not a residual image remains based on a change over time of the statistical value. Alternately, the image analyzing unit 109 determines whether or not a residual image remains based on a dose of applied radiation at the time of radiation application and a residual image attenuation characteristic acquired in advance.

In the radiation imaging system according to this embodiment, in Step S27 of FIG. 2, the information outputting unit 108 acquires the monitoring information from the image analyzing unit 109. Further, the information outputting unit 108 acquires from the monitoring unit 106, as the monitoring information, the length of time that has elapsed since the radiation imaging apparatus 1 acquired the offset correction data, the length of time that has elapsed since the radiation imaging apparatus 1 captured the exposure image, and the length of time that has elapsed since the radiation imaging apparatus 1 captured the non-exposure image.

Figure 8:
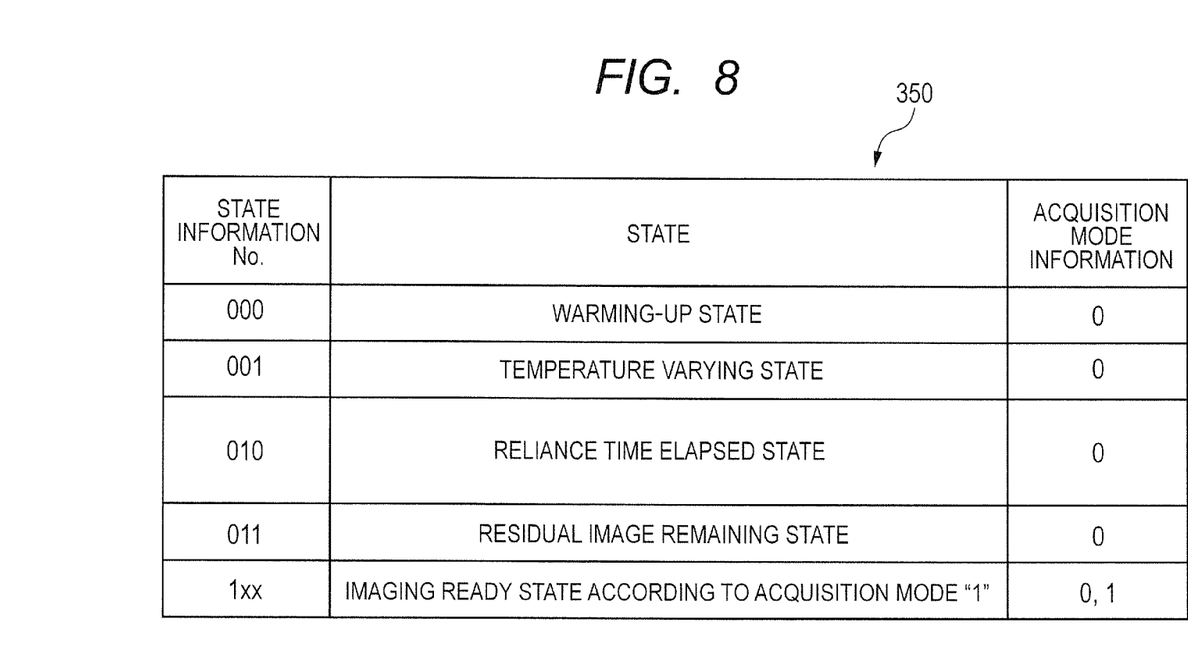
FIG. 8 is a table for showing an example of state information according to the second embodiment.

In Step S28, based on the monitoring information acquired in Step S27, the information outputting unit 108 outputs to the control apparatus 3 the state information on the state of the radiation imaging apparatus 1. FIG. 8 is a table for showing an example of the state information. State information 350 of FIG. 8 includes the state information No. and the state of the radiation imaging apparatus 1.

For example, based on the length of time that has elapsed since the radiation imaging apparatus 1 acquired the offset correction data (non-exposure image data), the information outputting unit 108 outputs the state information 350 including the reliance time elapsed state of the offset correction data (Step S28).

When a predetermined period of time (reliance time) has elapsed since the offset correction data (non-exposure image data) was acquired, reliability of the offset correction data decreases due to, for example, a temperature change of the radiation imaging apparatus 1. Therefore, when the length of time that has elapsed since the radiation imaging apparatus 1 acquired the offset correction data (non-exposure image data) is equal to or greater than a predetermined threshold, the information outputting unit 108 outputs the state information 350 including the reliance time elapsed state of the offset correction data.

In this case, the information outputting unit 108 may output the acquisition mode "0" corresponding to the reliance time elapsed state of the offset correction data as the acquisition mode information. Then, when the acquisition mode set by the control unit 103 is "1", the information outputting unit 108 may output the notice information, and as illustrated in FIG. 6, the warning 330 may be displayed, in which the screen for choosing the acquisition mode is displayed (Step S29).

Alternatively, based on the length of time that has elapsed since the radiation imaging apparatus 1 captured the exposure image or how much a residual image remains in the image captured by the radiation imaging apparatus 1 (the degree of the residual image), the information outputting unit 108 outputs the state information 350 including the residual image remaining state (Step S28).

When the length of time that has elapsed since the exposure image was captured is within a predetermined length of time, a residual image remains in the image captured by the radiation imaging apparatus 1. Therefore, when the length of time that has elapsed since the radiation imaging apparatus 1 captured the exposure image is less than a predetermined threshold, the information outputting unit 108 outputs the state information 350 including the residual image remaining state. Alternatively, based on the monitoring information acquired from the image analyzing unit 109, the information outputting unit 108 outputs the state information 350 including the residual image remaining state.

In this case, the information outputting unit 108 may output the acquisition mode "0" corresponding to the residual image remaining state as the acquisition mode information. Then, when the acquisition mode set by the control unit 103 is "1", the information outputting unit 108 may output the notice information, and as illustrated in FIG. 6, the warning 330 may be displayed, in which the screen for choosing the acquisition mode is displayed (Step S29).

As described above, by outputting the state information on the state of the radiation imaging apparatus to choose the acquisition mode, even when a residual image remains in an image, the imaging based on the image quality, the frame rate, or the like desired by the user is enabled. As a result, the usability for the user can be enhanced.

Therefore, in the radiation imaging apparatus according to the present invention, even when the state of the radiation imaging apparatus changes, the imaging based on the image quality, the frame rate, or the like desired by the user can be performed. As a result, the usability for the user can be enhanced.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-125086, filed Jun. 22, 2015, which is hereby incorporated by reference herein in its entirety.

What is claimed is:

1. A radiation imaging apparatus comprising a processor coupled to a storage medium programmed to function as:
   a mode setting unit configured to set an imaging mode for radiation imaging;
   an information outputting unit configured to output state information on a state of the radiation imaging apparatus;
   a correction data acquiring unit configured to acquire offset correction data through use of image data acquired in an acquisition mode;
   an image processing unit configured to correct image data acquired by imaging an object through use of the offset correction data; and
   a control unit configured to, when the acquisition mode based on the imaging mode coincides with the acquisition mode based on the state information, control the correction data acquiring unit to acquire the offset correction data in the acquisition mode based on the state information.

2. The radiation imaging apparatus according to claim 1, wherein the information outputting unit is configured to output the state information on the state of the radiation imaging apparatus based on temperature of the radiation imaging apparatus.

3. The radiation imaging apparatus according to claim 1, wherein the information outputting unit is configured to output the state information on the state of the radiation imaging apparatus based on a length of time that has elapsed since the radiation imaging apparatus was powered on.

4. The radiation imaging apparatus according to claim 1, wherein the information outputting unit is configured to output the state information on the state of the radiation imaging apparatus based on at least one of a length of time that has elapsed since the radiation imaging apparatus acquired the offset correction data, a length of time that has elapsed since the radiation imaging apparatus captured an exposure image, or a length of time that has elapsed since the radiation imaging apparatus captured a non-exposure image.

5. The radiation imaging apparatus according to claim 1, wherein the information outputting unit is configured to output the state information on the state of the radiation imaging apparatus based on how much a residual image remains in an image captured by the radiation imaging apparatus.

6. The radiation imaging apparatus according to claim 1, wherein the information outputting unit is configured to output, as the state information, at least one of a warming-up state, an equilibrium state, a temperature varying state, an imaging ready state according to a predetermined acquisition mode, a reliance time elapsed state of the offset correction data, or a residual image remaining state of the radiation imaging apparatus.

7. The radiation imaging apparatus according to claim 1, wherein the control unit is configured to, when the acquisition mode based on the imaging mode and the acquisition mode based on the state information are different from each other, output notice information for notifying that the acquisition modes are different from each other.

8. The radiation imaging apparatus according to claim 1, wherein the information outputting unit is configured to set a threshold based on a temperature change of the radiation imaging apparatus and to compare temperature of the radiation imaging apparatus to the threshold, to thereby output the state information.

9. A radiation imaging apparatus comprising a processor coupled to a storage medium programmed to function as:
   an information outputting unit configured to output state information on a state of the radiation imaging apparatus including temperature of the radiation imaging apparatus;
   a correction data acquiring unit configured to acquire offset correction data through use of image data acquired in an acquisition mode that is set based on the state information; and
   an image processing unit configured to correct image data acquired by imaging an object through use of the offset correction data,
   wherein the information outputting unit is configured to output, as the acquisition mode information based on the state information, an acquisition mode of acquiring the offset correction data through the use of the image data acquired in advance before the imaging of the object, and
   wherein the correction data acquiring unit is configured to acquire the offset correction data based on the acquisition mode.

10. A radiation imaging apparatus comprising a processor coupled to a storage medium programmed to function as:
    an information outputting unit configured to output state information on a state of the radiation imaging apparatus including temperature of the radiation imaging apparatus;
    a correction data acquiring unit configured to acquire offset correction data through use of image data acquired in an acquisition mode that is set based on the state information; and
    an image processing unit configured to correct image data acquired by imaging an object through use of the offset correction data,
    wherein the information outputting unit is configured to output, as the acquisition mode information based on the state information, an acquisition mode of alternately performing the imaging of the object and the acquisition of the offset correction data through use of the image data acquired after the imaging of the object, and
    wherein the correction data acquiring unit is configured to acquire the offset correction data based on the acquisition mode.

11. The radiation imaging apparatus according to claim 1, wherein the correction data acquiring unit is configured to acquire the offset correction data through use of a plurality of pieces of the image data.

12. A radiation imaging system comprising:
    a radiation imaging apparatus comprising a processor coupled to a storage medium programmed to function as:
      an information outputting unit configured to output state information on a state of the radiation imaging apparatus;
      a correction data acquiring unit configured to acquire offset correction data through use of image data acquired in an acquisition mode that is set based on the state information; and
      an image processing unit configured to correct image data acquired by imaging an object through use of the offset correction data;
    a radiation generating apparatus configured to apply radiation to the radiation imaging apparatus;
    a control apparatus configured to:
      set the acquisition mode; and
      display, to a display, a notice of notice information regarding that the acquisition mode that is based on the state information and the acquisition mode that is set for the radiation imaging apparatus are different from each other, and GUI for resetting of the acquisition mode on the same screen.

13. The radiation imaging system according to claim 12, wherein the control apparatus is configured to display an imaging preparation completion notice, the state information and the notice information.

14. The radiation imaging apparatus according to claim 1, wherein the offset correction data is acquired from the image data before or after the imaging of the object, according to the acquisition mode.

15. The radiation imaging apparatus according to claim 1, wherein, when the acquisition mode based on the imaging mode does not coincide with the acquisition mode based on the state information, the control unit configured to control the correction data acquiring unit to acquire the offset correction data in a selected one among the acquisition modes based on the imaging mode and the state information.

* * * * *